United States Patent
Scifert et al.

(10) Patent No.: US 6,746,487 B2
(45) Date of Patent: Jun. 8, 2004

(54) INTRAMEDULLARY TRIAL FIXATION DEVICE

(75) Inventors: Christopher Scifert, Bartlett, TN (US); Dean Hughes, Cordova, TN (US); Scott Elliott, Memphis, TN (US)

(73) Assignee: Smith & Nephew, Inc., Memphis, TN (US)

(*) Notice: Subject to any disclaimer, the term of this patent is extended or adjusted under 35 U.S.C. 154(b) by 65 days.

(21) Appl. No.: 10/091,817

(22) Filed: Mar. 6, 2002

(65) Prior Publication Data

US 2003/0171816 A1 Sep. 11, 2003

(51) Int. Cl.$^7$ .................................................. A61F 2/32
(52) U.S. Cl. ................................. 623/22.12; 623/22.11; 606/86
(58) Field of Search .......................... 623/22.12, 22.35, 623/22.41, 22.11, 23.44, 18.11, 23.11, 908, 19.11, 19.14; 606/86, 87, 95, 98, 99, 102, 104

(56) References Cited

U.S. PATENT DOCUMENTS

| | | | |
|---|---|---|---|
| 3,694,820 A | | 10/1972 | Scales et al. |
| 3,803,641 A | | 4/1974 | Golyahovsky |
| 4,045,825 A | | 9/1977 | Stroot |
| 4,106,130 A | | 8/1978 | Scales |
| 4,179,758 A | | 12/1979 | Gristina |
| 4,865,605 A | | 9/1989 | Dines et al. |
| 4,881,536 A | * | 11/1989 | Noble et al. .................. 606/94 |
| 4,919,670 A | | 4/1990 | Dale et al. |
| 5,035,717 A | * | 7/1991 | Brooks ..................... 623/23.44 |
| 5,064,427 A | * | 11/1991 | Burkinshaw ................. 606/99 |
| 5,358,526 A | | 10/1994 | Tornier |
| 5,462,563 A | | 10/1995 | Shearer et al. |
| 5,489,309 A | | 2/1996 | Lackey et al. |
| 5,549,682 A | | 8/1996 | Roy |
| 5,702,457 A | | 12/1997 | Walch et al. |
| 5,876,459 A | * | 3/1999 | Powell ..................... 623/23.15 |
| 5,906,644 A | * | 5/1999 | Powell ..................... 623/20.15 |
| 5,961,555 A | | 10/1999 | Huebner |
| 6,102,953 A | * | 8/2000 | Huebner ................... 623/19.11 |
| 6,120,507 A | | 9/2000 | Allard et al. |

(List continued on next page.)

FOREIGN PATENT DOCUMENTS

| | | |
|---|---|---|
| EP | 0 679 375 A1 | 11/1995 |
| EP | 0 712 617 A1 | 5/1996 |
| EP | 0 679 375 B1 | 9/1998 |
| EP | 0 712 617 B1 | 9/1999 |
| EP | 0 940 126 A1 | 9/1999 |
| EP | 1 048 274 A2 | 11/2000 |
| EP | 1 082 943 A2 | 3/2001 |
| FR | 2 664 809 | 1/1992 |
| WO | WO 96/17553 | 6/1996 |

OTHER PUBLICATIONS

Smith & Nephew Orthopaedics Brochure "Performance, Innovation, Trust—Neer 3™ Surgical Technique for Fractures," by Professor Michel Mansat, Toulouse, France, pp. 1–15 (Sep. 2000).

*Primary Examiner*—Pedro Philogene
(74) *Attorney, Agent, or Firm*—Kilpatrick, Stockton LLP

(57) ABSTRACT

An intramedullary fixation device for use in securing a trial in the medullary canal of a bone to determine the offset and orientation of a prosthetic implant for replacement of a joint articulating surface of the bone is disclosed. The fixation device comprises a body for receiving a trial and a fixation portion for engaging the trial. A system for use in surgical repair of a joint comprising a selection of prosthetic implants of various sizes, a selection of trials of various sizes corresponding to the sizes of the implants, a selection of fixation devices of various sizes corresponding to the sizes of the trials, a trial fixation device driver for inserting the fixation device and attached trial into the canal of a bone, and a trial device extractor for removing the fixation device from the resected bone is disclosed. Methods of using the fixation device and system of the invention are disclosed.

51 Claims, 7 Drawing Sheets

U.S. PATENT DOCUMENTS

| | | |
|---|---|---|
| 6,168,627 B1 | 1/2001 | Huebner |
| 6,168,628 B1 | 1/2001 | Huebner |
| 6,193,758 B1 | 2/2001 | Huebner |
| 6,197,063 B1 | 3/2001 | Dews |
| 6,203,575 B1 | 3/2001 | Farey |
| 6,228,120 B1 | 5/2001 | Leonard et al. |
| 6,277,123 B1 | 8/2001 | Maroney et al. |
| 6,283,999 B1 | 9/2001 | Rockwood, Jr. |
| 6,428,578 B2 * | 8/2002 | White .................... 623/23.22 |

* cited by examiner

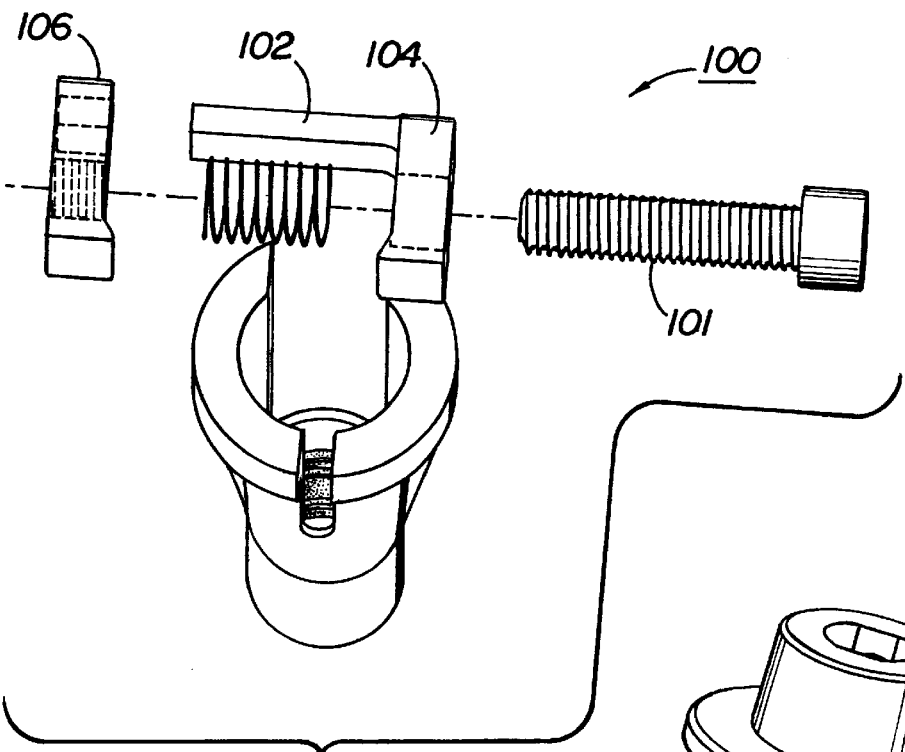
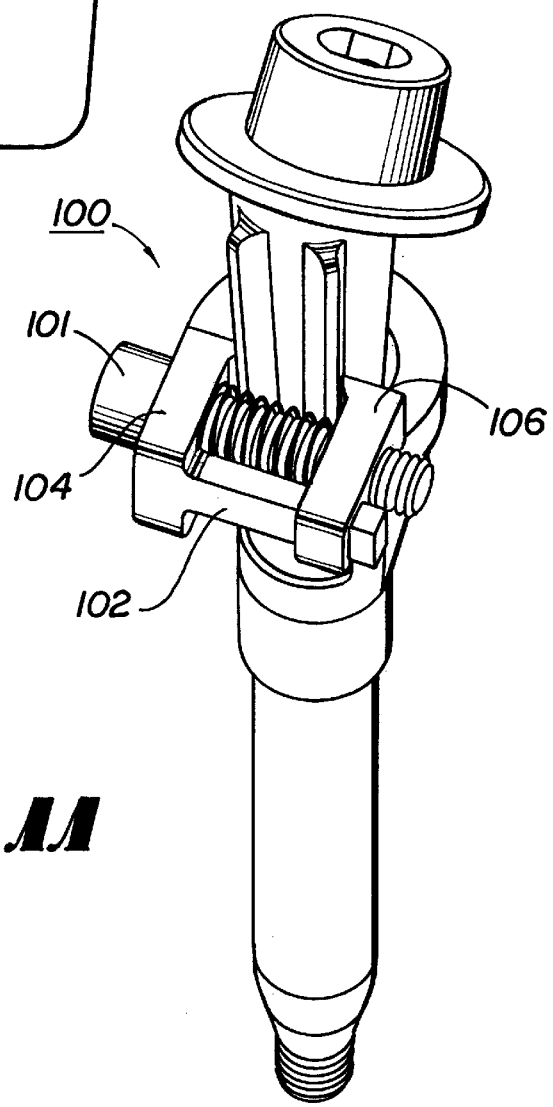
FIG. 10
FIG. 11

INTRAMEDULLARY TRIAL FIXATION DEVICE

FIELD OF THE INVENTION

The present invention relates to a prosthetic system for joint replacement, and more particularly to a trial fixation device for securing a trial in the medullary canal of a resected bone so that accurate measurements can be made for fitting a prosthetic implant.

BACKGROUND

Patients suffering from trauma or disorders causing severe joint pain often require surgical treatment involving complete or partial replacement of the affected joint. For example, prostheses for replacing all or a portion of a damaged or diseased knee, hip, and shoulder of a person are well known.

When reconstructing damaged or diseased joints with an artificial prosthesis, it is desirable to position the components of the prosthesis such that the structure and function of the properly functioning natural joint is replicated to the greatest degree possible. This involves consideration of several factors. For example, the components of the prosthesis must be inserted such that the patient has the desired limb length after surgery. It is also desirable that the range of motion of the joint after surgery is, to the extent possible, the same as that of a healthy joint. Some of the factors relevant to proper placement include insertion depth of the prosthesis components into the bone and rotational orientation of the prosthesis components.

During a shoulder replacement operation, at least a portion of the proximal section of the humeral shaft is replaced by a metal prosthesis. This prosthesis generally consists of two parts: a stem that is mounted into the medullary canal of the humerus, and a head component connected in some manner to the stem. The head component replaces the bearing surface of the humerus and articulates within the glenoid cavity of the scapula to allow movement of the shoulder. An example of a humeral prosthetic system is the Neer 3 System from Smith & Nephew, Inc.

The stem and head component of a humeral prosthesis may be supplied in "modular" form, that is, as separate connectable components. Different stem sizes and head sizes in a modular implant design provide the surgeon with some degree of flexibility, which facilitates reconstruction of the original anatomy of the patient.

With a range of stem sizes and a range of head sizes available, the surgeon can choose a particular combination to suit the anatomy of each individual patient without having a large inventory of "integral" or "monoblock" humeral prostheses. For example, one patient may require a relatively small head and a relatively long stem. With a monoblock prosthesis, a wide range of stem lengths and/or diameters are required for each head size, whereas with a modular arrangement, a particular head may be used with a range of stem, sizes, and a particular stem may be used with a variety of head sizes.

Additional variations also arise because individual patients may require differing angles of inclination of the head relative to the stem and differing eccentricities between the axis of the head and the axis of the stem. Thus, for example, in one patient, the eccentricity may be posterior and in another patient, it may be anterior.

Various shoulder prostheses are disclosed in European Patent Publication No. EP-A 0 679 375; EP-A 0 712 617; French Patent No. FR-A 2 664 809; U.S. Pat. Nos. 3,694,820; 3,803,641; 4,045,825; 4,106,130; 4,179,758; 4,865,605; 4,919,670; 5,358,526; 5,549,682; 5,462,563 and 5,702,457; and PCT International Patent Publication No. WO 96/17553, the entirety of which are hereby incorporated by reference.

Before surgery to reconstruct a patient's shoulder with a humeral prosthesis, x-rays and x-ray templates are used to give an indication of the necessary height and size of the prosthesis. During surgery trial stems and heads are used by the surgeon to choose the appropriate offset height and retroversion for the humeral prosthesis. The trial stem is inserted into the medullary canal, the trial head is attached (in the case of a modular trial), and the shoulder is taken through a range of motion. The trial stem may be graduated at 5 mm intervals to facilitate the determination of the proper height for stem implantation. Typically, an alignment rod is used to check retroversion.

The trial implant position is critical for restoring the height of the humerus and the degree of retroversion. The height of the humerus effects the balance of the soft tissues. The soft tissues are attached to the prosthesis in a balanced manner to avoid subluxation and for a good range of motion. If the offset is too high, then the soft tissue tension is too tight and if the offset is too low, then the soft tissue tension is too lax.

In order to accurately test the correct height of the trial stem, the trial stem is held in place in the medullary canal. Current methods of securing the trial stem in the medullary canal include packing gauze in the medullary canal around the trial stem to keep it in position. This method does not allow the surgeon an easy way to adjust the height, if the trial stem is found to be at the incorrect height, or provide a reliable method of keeping the trial stem in place during the range of motion test.

Another method is to use an extramedullary device to hold the trial stem in place. These extramedullary devices are big and bulky and prevent an effective range of motion being investigated during surgery and do not allow the surgeon to close the tuberosities and other soft tissue around the trial stem in order to check the balance of soft tissues.

SUMMARY

Methods, devices, and systems of this invention seek to provide a trial fixation device for use in complete or partial joint replacement and repair that secures a trial in the medullary canal of a bone. With the trial fixation device of the invention, the trial can be securely fixed in the bone canal, the trial can be put through a full range of motion, the balance of the soft tissues can be tested, and the height of the trial can easily be adjusted if necessary.

Methods, devices, and systems according to this invention more particularly provide an intramedullary trial fixation device designed to engage a trial and secure the trial in the canal of a bone, a prosthetic system for replacement or repair of all or a portion of the damaged joint, and methods for using the intramedullary trial fixation device to replace or repair a damaged joint. In one embodiment, the primary components of the trial fixation device are a body adapted to be received in the resected bone and adapted to receive a trial stem and a fixation portion attached to the body for engaging the trial stem.

An additional aspect of this invention is a surgical system that includes a selection of prosthetic implants of various sizes and shapes, a corresponding selection of trial prostheses, a corresponding selection of fixation devices, and a selection of devices for implanting and removing the fixation device.

Another aspect of this invention seeks to provide a method of using the trial fixation device for replacing or repairing all or a portion of a damaged joint and orienting the prosthesis to compliment the patient's natural anatomy. More particularly, this invention provides a method of replacing the proximal humerus and humeral head.

These and other features of this invention will become apparent after a review of the following detailed description of the disclosed embodiments.

BRIEF DESCRIPTION OF THE DRAWINGS

FIG. 10 is an exploded view of another embodiment of a fixation device of the invention.

FIG. 11 is a perspective view showing the fixation device of FIG. 10 engaging a trial stem.

DETAILED DESCRIPTION

Methods, systems and devices according to embodiments of this invention seek to provide improved trialing during complete and partial joint replacement and repair. A trial fixation device of this invention may include a device that engages and secures a trial in a bone canal, such as a device including a body adapted to be received in a resected bone and a fixation portion attached to the body for engaging a trial stem. In one embodiment of this invention, the fixation portion comprises a first capture member attached to the body, a second capture member, and a first fastener adapted to move the second capture member towards the first capture member to engage the trial stem. The first capture member has a first aperture, the second capture member has a second threaded aperture, and the first fastener is a first tension bolt adapted to extend through the first aperture and thread through the second aperture so that when the first tension bolt is tightened, the second capture member moves toward the first capture member. The first capture member has a third threaded aperture and the second capture member has a fourth aperture and the device further includes a second tension bolt adapted to extend through the fourth aperture and thread through the third aperture so that when the second tension bolt is tightened the second capture member moves toward the first capture member to engage the trial stem.

Figure 1:
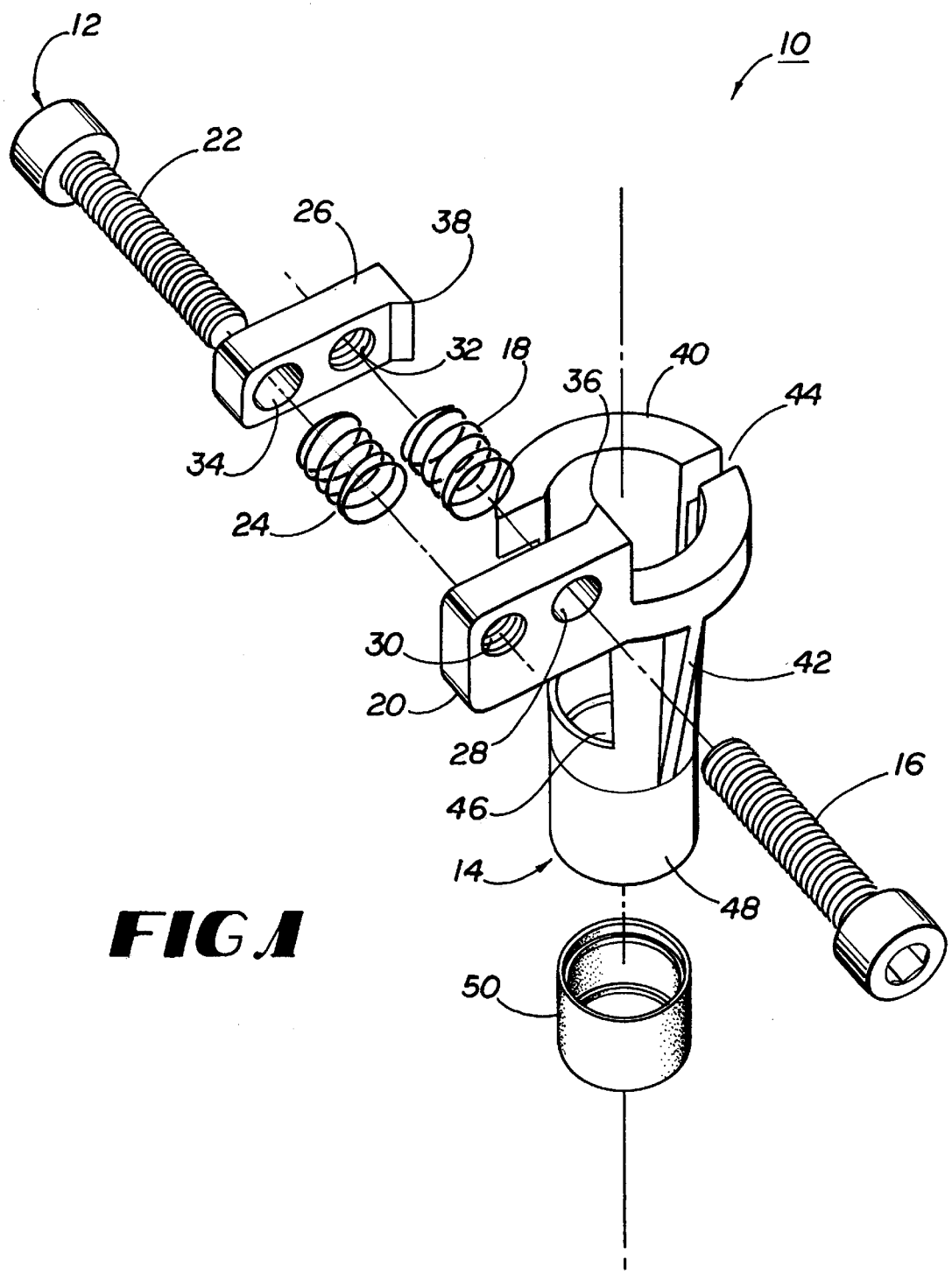
FIG. 1 is an exploded view of a fixation device according to one embodiment of this invention.
Figure 2:
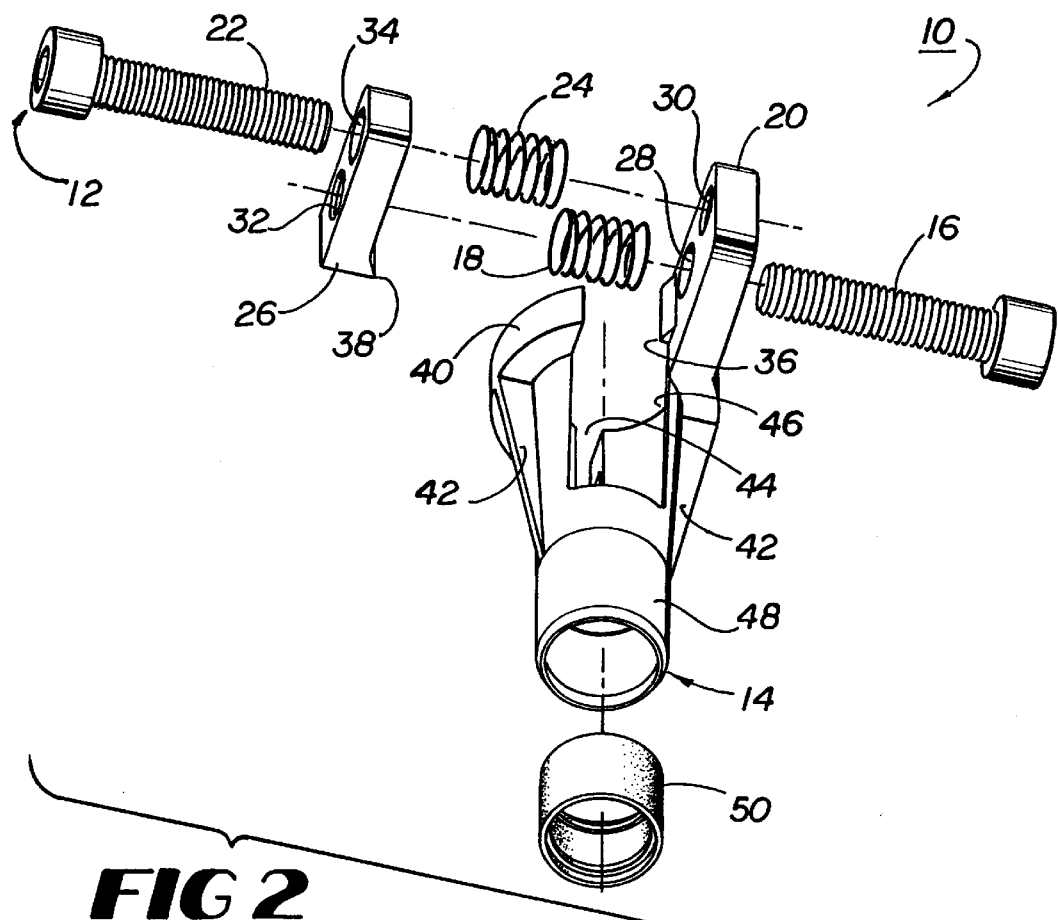
FIG. 2 is another exploded perspective view of the fixation device of FIG. 1.
Figure 3:
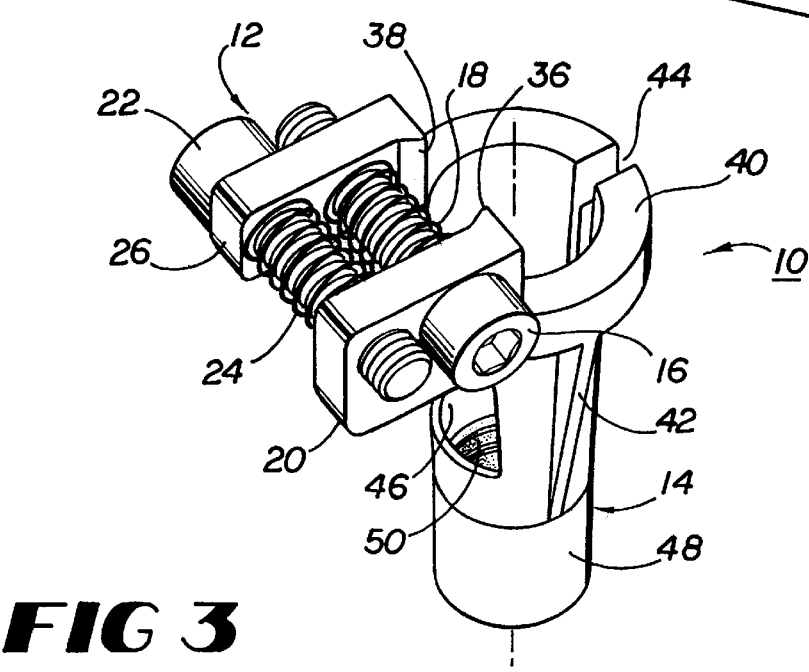
FIG. 3 is a perspective view of the fixation device of FIG. 1.
Figure 4:
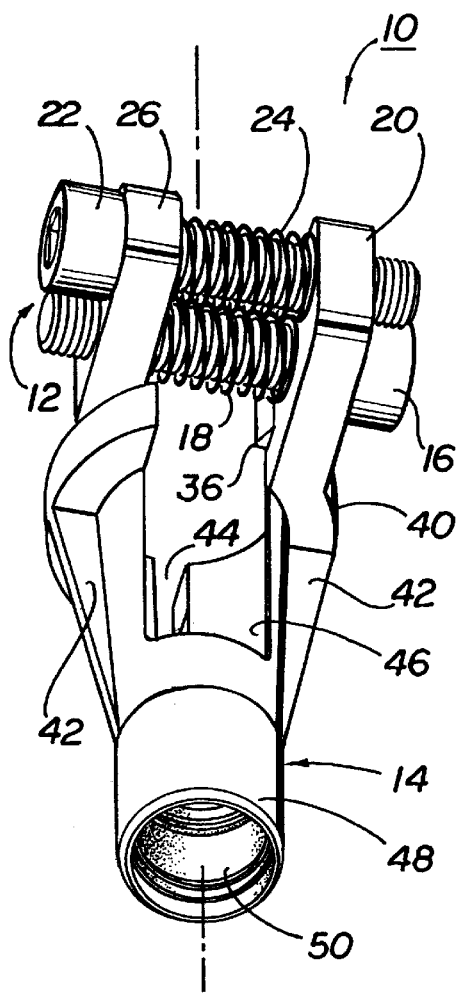
FIG. 4 is another perspective view of the fixation device of FIG. 1.

Consider one example of a device according to one embodiment of this invention. FIGS. 1 and 2 illustrate an exploded view of an intramedullary trial fixation device 10 according to one embodiment of the present invention. FIGS. 3 and 4 illustrate perspective views of the trial fixation device 10. The trial fixation device 10 includes a fixation portion 12 and a body 14. The fixation portion 12 includes a first fastener 16, a first bias 18, a first capture member 20, a second fastener 22, a second bias 24, and a second capture member 26.

The first capture member 20 has two apertures—an inner, smooth aperture 28 and an outer, threaded aperture 30. The second capture member 26 has two apertures—an inner, threaded aperture 32 and an outer, smooth aperture 34. The capture members 20, 26 have opposite fingers 36, 38 at the inner end of each capture member.

The first capture member is attached to a collar 40 on the body 14. The second capture member 26 is not attached to the body 14 and its position is determined by the fasteners 16, 22. The fasteners 16, 22 in the embodiment shown in FIGS. 1–4 are tension bolts. In other embodiments, any suitable fastener may be used. As shown in FIGS. 3 and 4, the first fastener 16 extends through the inner, smooth aperture 28 and is threaded in the inner, threaded aperture 32. The second fastener 22 extends through the outer, smooth aperture 34 and is threaded in the outer, threaded aperture 30.

Tightening either fastener moves the second capture member 26 toward the first capture member 20 and loosening either fastener moves the second capture member 26 away from the first capture member 20. As the first fastener 16 is tightened or loosened, the second fastener 22 slides through the outer, smooth aperture 34. As the second fastener 22 is tightened or loosened, the first fastener 16 slides through the inner, smooth aperture 28. For example, when the first fastener 16 is tightened the outer, smooth aperture 34 of the second capture member 26 slides over the second fastener 22 allowing the second capture member 22 to move closer to the first capture member 20. The first bias 18 and second bias 24 are placed around the fasteners 16, 22 between the capture members 20, 26 and serve to keep the second capture member 26 from becoming loose and sliding back and forth. In the embodiment of FIGS. 1–4, the biases 18, 24 are compression springs. In other embodiments, any suitable biasing element may be used.

While above described embodiment of the fixation portion 12 uses two fasteners, one of skill in the art understands that one fastener could be used. FIGS. 10 and 11 illustrate an embodiment of a fixation device 100 using one fastener 101, in the illustrated embodiment, a tension bolt. As shown in FIGS. 10 and 11 a capture member connector 102 is attached to the first capture member 104 and slidably extends through an outer aperture on the second capture member 106. The capture member connector 102 adds stability to the fixation portion.

The fixation portion illustrated in the Figures is designed to work with the Neer 3 and Modular Neer 3 trial stems from Smith & Nephew, Inc. One of skill in the art understands that the fixation portion could be configured a variety of different ways to secure a Neer 3 or Modular Neer 3 trial stem and different trial stems to the fixation device. For example, a radially compressing semi-circular clamp fitting within the collar at the top of the device could close around the diameter of the implant, thereby providing fixation. Also, a tight fitting but compressible liner could be used in the distal portion of the device to control height, rather than a clamping mechanism. Also, a clamping mechanism devised to attach to the medial fixation fin rather than the lateral fixation fin could be used to attach the device to the trial stem.

As shown in FIGS. 1–4, the body includes a collar 40 around the proximal end to which the fixation portion 12 is connected. Two rotation prevention fins 42 extend from the collar 40 down the sides of the body 14. The proximal section of the body 14 includes a medial trial fin slot 44 and a lateral trial fin slot 46. The distal end of the body includes a trial stem sleeve 48. In one embodiment, a friction liner 50 is affixed to the interior surface of the trial stem sleeve 48. In one embodiment, the friction liner 50 is made of plastic, but in other embodiments may be made of any suitable material. One of skill in the art understands that the body can be configured a variety of different ways to accommodate a Neer 3 trial stem or different trial stems.

The preferred method of manufacturing the fixation device is machining. Although other methods, such as casting, could be used.

Figure 5:
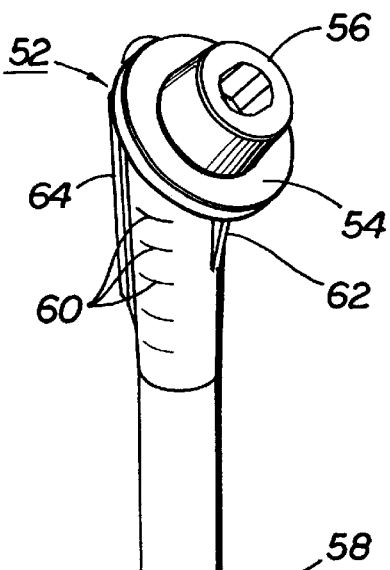
FIG. 5 is an exploded view of a trial stem and the fixation device of FIG. 1.

FIG. 5 illustrates an exemplary intramedullary humeral trial stem 52 that can be used with the intramedullary trial fixation device. The trial stem 52 includes a humeral trial head plateau 54 with a humeral trial head attachment post 56 affixed on the proximal side of the plateau. A humeral trial head (not shown) is attached to the humeral trial head attachment post 56 for modular trial stems. Monoblock trial stems have an attached humeral trial head.

A stem 58 is formed on or affixed to the distal side of the humeral head plateau 54. The proximal end of the stem 58 may have graduated laser markings 60 to allow for stem positioning in the humerus. A medial fin 62 extends from the distal side of the humeral head plateau 54 to the stem 58. Two lateral fins 64 are included on the stem opposite the medial fin 62. The lateral fins 64 and the medial fin 62 replicate the fixation fins on a humeral prosthetic implant.

Figure 6:
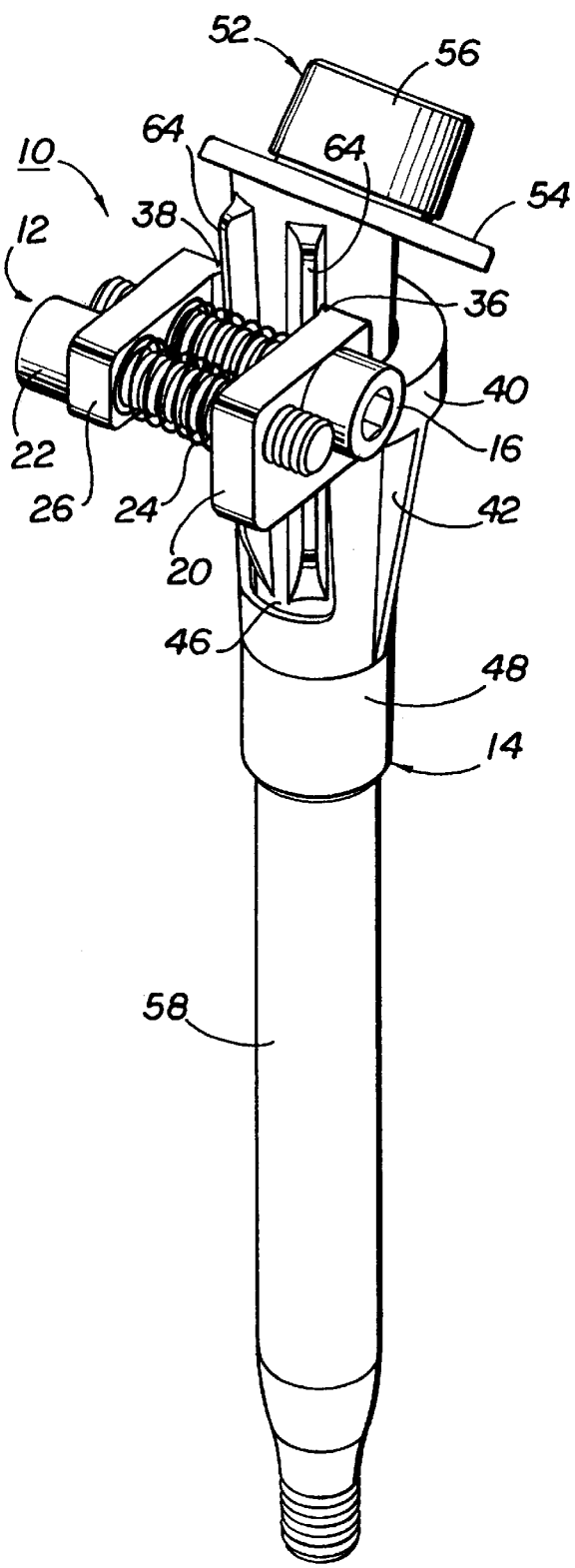
FIG. 6 is a perspective view showing the fixation device and trial stem of FIG. 5, as engaged.
Figure 7:
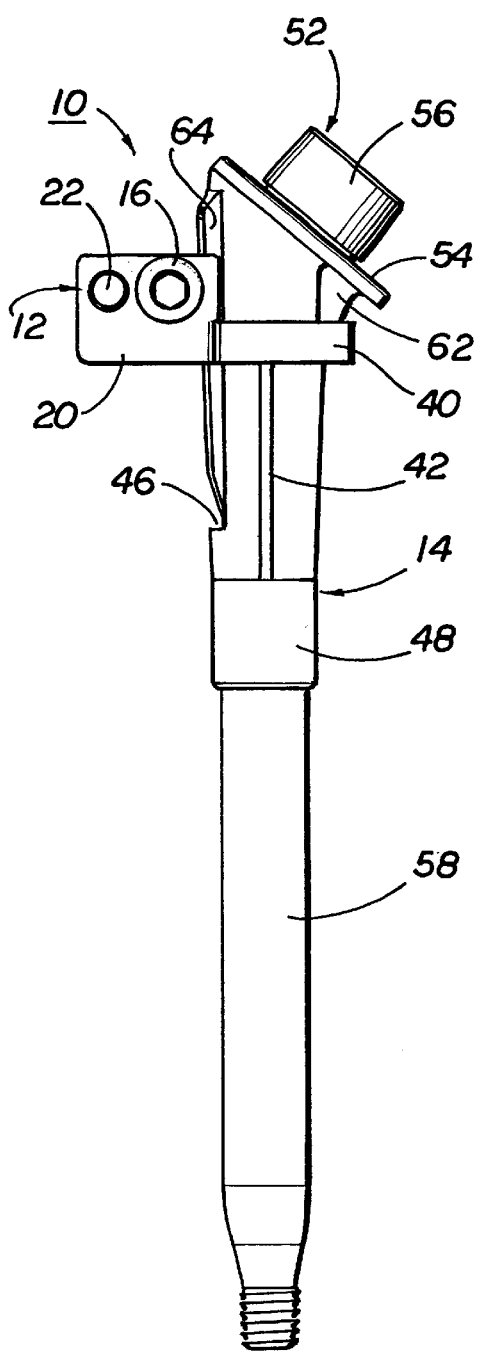
FIG. 7 is a side view of the fixation device and the trial stem of FIG. 5.

FIGS. 6 and 7 illustrate an embodiment of the fixation device 10 engaging the trial stem 52. The trial is secured in the fixation device 10 by locking the fixation portion 12 on the trial stem 52. In the embodiment shown in FIGS. 6 and 7, the trial is inserted into the fixation device 10 through the trial stem sleeve 48 so that the fingers 36, 38 of the capture members 20, 26 engage the lateral fins 64 of the trial stem 52 and the friction liner 50 engages the stem 58. The lateral fins 64 of the trial stem 52 fit in the lateral trial fin slot 46 and the medial fin 62 of the trial stem 52 fit in the medial trial fin slot 44. The friction liner 50 keeps the height of the trial stem 52 constant until the fixation portion 12 engages the trial stem 52. The position of the trial stem 52 is adjusted by unlocking the fixation portion 12, moving the trial stem 52, and locking the fixation portion 12 to re-engage the trial stem 52.

Figures 8, 9:
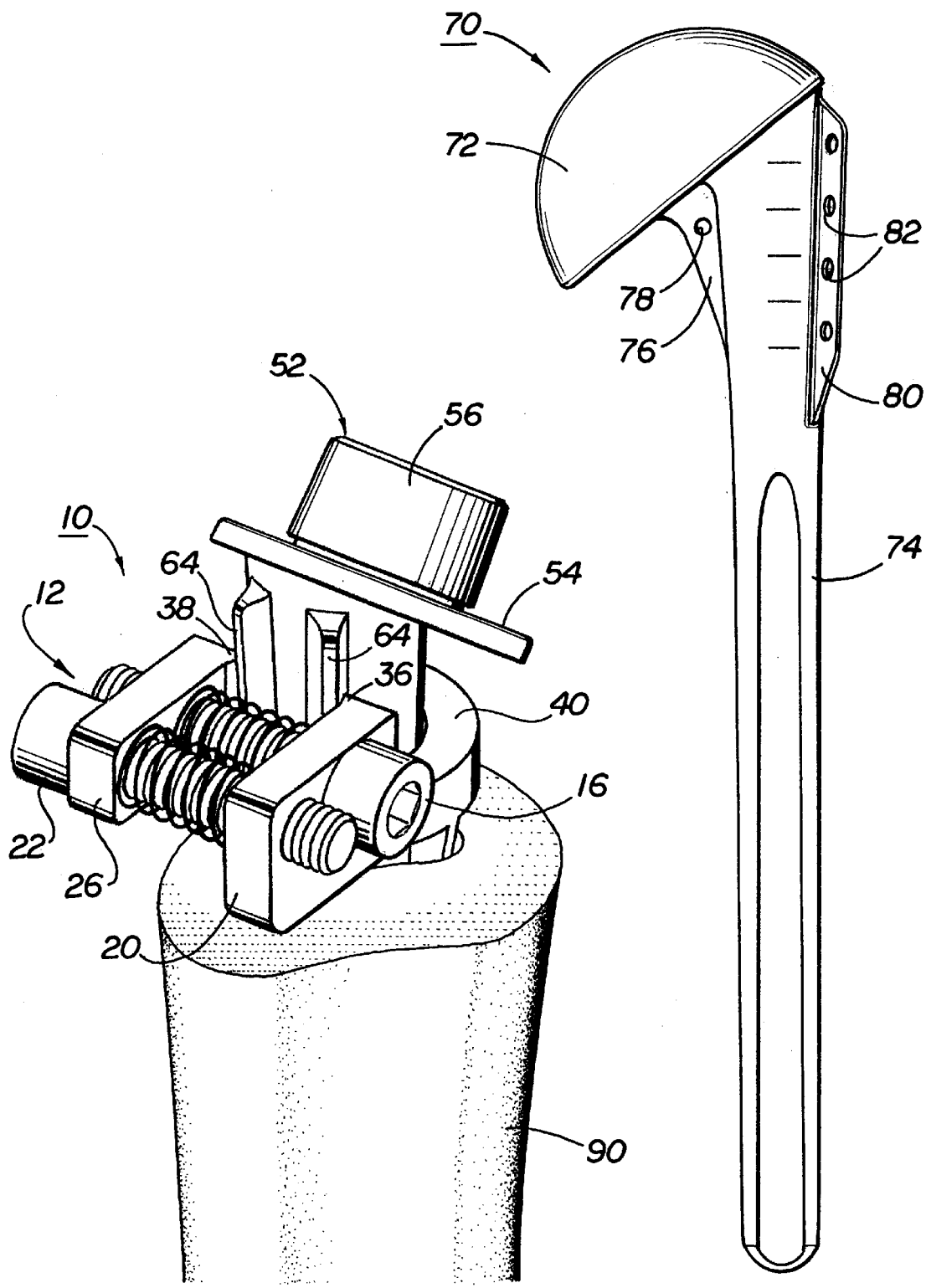
FIG. 8 is a perspective view of the trial stem and the fixation device of FIGS. 6–7 implanted in the medullary canal of a bone.
FIG. 9 is a side view of a prosthetic implant according to one embodiment of this invention.

FIG. 9 illustrates an exemplary humeral prosthetic implant 70. The prosthesis has a humeral head 72 and a stem 74 extending from the head. The prosthetic implant 70 could be modular or monoblock. A medial fixation fin 76 extends from the humeral head to the stem and includes a fixation hole 78. Two lateral fixation fins 80 are formed on the proximal part of the stem 74. The lateral fixation fins are in a sixty degree angle to each other positioned in a way that they align with the bicipital groove, giving the correct retroversion for the prosthesis. The lateral fixation fins each have four holes 82 allowing for the anatomical fixation of the tuberosities with sutures.

Figure 12:
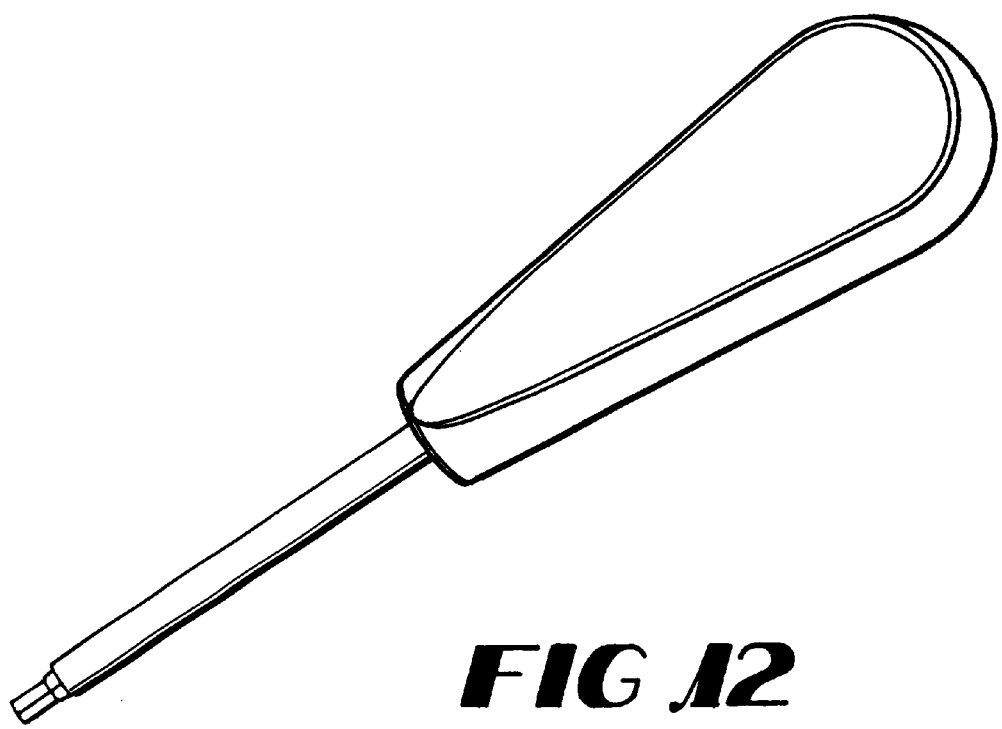
FIG. 12 is a perspective view of a trial fixation device driver according to one embodiment of this invention.

In cases of three or four part fractures of the proximal humerus or severe osteoarthritis, a humeral prosthetic implant like the one illustrated in FIG. 9 and described above is used to repair the shoulder. Initially, during surgery the humerus is prepared according to established surgical technique, which may include resecting the proximal portion and may include reaming the medullary canal. An appropriate trial stem is placed into the fixation device. The fixation portion of the fixation device is locked onto the trial stem. As shown in FIG. 8, the fixation device 10 and attached trial stem 52 are introduced into the medullary canal until the collar of the fixation device is flush, or as close as possible, to the bony surface of the humerus 90. A trial fixation device driver can be used to lock the fixation device to the trial stem. FIG. 12 illustrates an embodiment of a trial fixation device driver. The fixation portion 12 of the fixation device 10 is unlocked and the height of the trial stem 52 is adjusted to the desired position based on the use of x-rays and x-ray templates before surgery. Once the trial stem 52 is adjusted to the desired position, the fixation portion 12 is locked onto the trial stem 52. The fixation device 10 illustrated in FIGS. 1–7 has two fasteners 16, 22 to allow easy access to the fasteners for use in left and right shoulder procedures.

Figure 13:
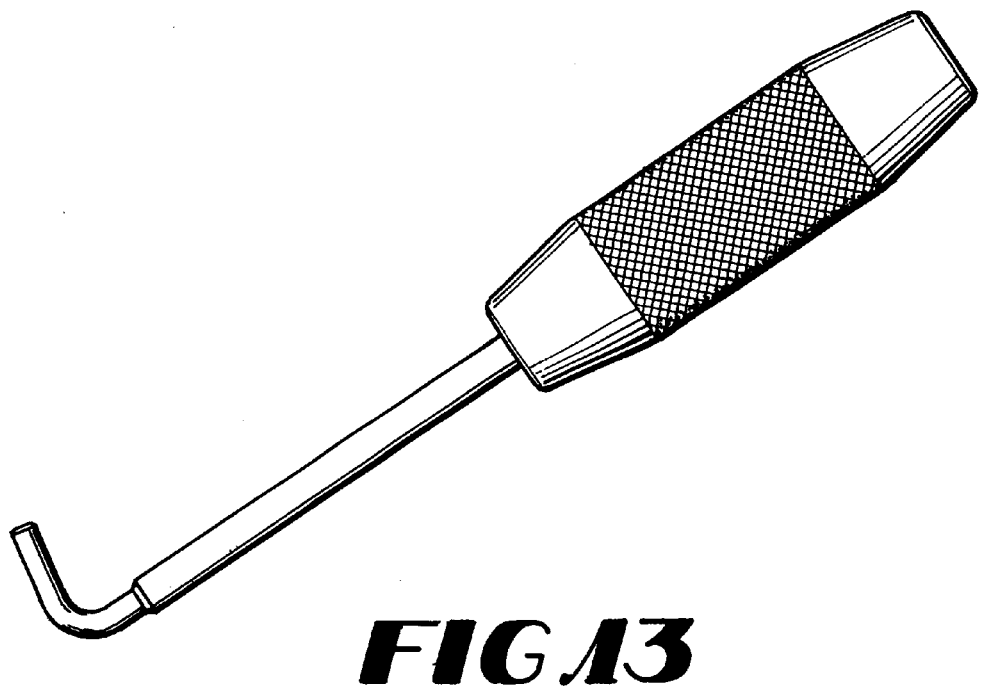
FIG. 13 is a perspective view of a trial fixation device extractor according to one embodiment of this invention.

A trial head is placed on the trial stem and the range of motion of the shoulder is evaluated. If the range of motion is satisfactory, the position of trial height is noted by observing the marks 60 on the trial stem in relation to the device or the surface of the humerus. If desired, the trial stem 52 is marked with a pen at the appropriate position. If the range of motion is not satisfactory, the fixation portion 12 is unlocked and the height of the trial stem 52 adjusted until an acceptable position is reached. The trial stem 52 and fixation device 10 are then removed. If the device 10 does not come out with the trial stem 52, a trial fixation device extractor can be used to lever the device out of the humerus. FIG. 13 illustrates an embodiment of the trial fixation device extractor. The humeral prosthesis is marked at the same position as the trial stem in order to indicate the correct offset for the prosthetic implant. Cement may be inserted medullary canal. The prosthetic implant 70 is placed in the canal at the marked height. The tuberosities and other soft tissue are then connected to the prosthetic implant.

The disclosure of devices and processes as recited above is not intended to limit the scope of the present invention. A person of skill in the art understands that various fixation portions can be used with different intramedullary fixation device body structures to accommodate different stem geometries. A person of skill in the art understands that, while the embodiments of the fixation device are described in terms of a prosthetic implant for a humerus, the fixation device could be used with other prosthetic devices.

What is claimed is:

1. An apparatus for securing a trial stem in the medullary canal of a bone, comprising:
   a) a body having a proximal end and a distal end, the body adapted to be received in the bone and adapted to receive the trial stem;
   b) a fixation portion attached to the body for engaging the trial stem; and
   c) a trial stem.

2. The apparatus of claim 1, wherein the fixation portion uses a clamping mechanism to engage the trial stem.

3. The apparatus of claim 1, wherein the fixation portion comprises:
   a first capture member attached to the body;

a second capture member; and a first fastener, wherein the first fastener is adapted to engage the second capture member and move the second capture member towards the first capture member to engage the trial stem.

4. The apparatus of claim 3, wherein the first capture member has a first aperture, the second capture member has a second threaded aperture, and the first fastener is a first tension bolt adapted to extend through the first aperture and thread through the second aperture so that when the first tension bolt is tightened, the second capture member moves toward the first capture member.

5. The apparatus of claim 4, wherein the first capture member comprises a first finger and the second capture member comprises a second finger and the trial stem is engaged between the first finger and the second finger.

6. The apparatus according to claim 5, wherein the trial stem has a first lateral fin and a second lateral fin and the first finger engages the first lateral fin and the second finger engages the second lateral fin.

7. The apparatus according to claim 3, further comprising a first bias interposed between the first and second capture members.

8. The apparatus according to claim 7, wherein the first bias is a first compression spring and is adapted to surround the first fastener.

9. The apparatus according to claim 4, wherein the first capture member has a third threaded aperture and the second capture member has a fourth aperture, the apparatus further comprising a second tension bolt adapted to extend through the fourth aperture and thread through the third aperture so that when the second tension bolt is tightened the second capture member moves toward the first capture member to engage the trial stem.

10. The apparatus according to claim 9, further comprising a second compression spring interposed between the first and second capture members and surrounding the second tension bolt.

11. The apparatus of claim 9, wherein the first capture member comprises a first finger and the second capture member comprises a second finger and the trial stem is engaged between the first finger and the second finger.

12. The apparatus according to claim 11, wherein the trial stem has a first lateral fin and a second lateral fin and the first finger engages the first lateral fin and the second finger engages the second lateral fin.

13. The apparatus according to claim 3, wherein the fixation portion further comprises a capture member connector connected to the first capture member, wherein the second capture member has a connector aperture adapted to slidably receive the capture member connector.

14. The apparatus according to claim 3, wherein the body comprises:
a collar at the proximal end;
a medial fin slot extending from the proximal end down the body;
a lateral fin slot extending from the proximal end down the body;
two rotation prevention fins extending from the collar down the body; and
a trial stem sleeve at the distal end having an interior surface.

15. The apparatus according to claim 14, further comprising a friction liner adapted to be affixed to the interior surface of the trial stem sleeve.

16. The apparatus of claim 1, wherein the body has a collar at the proximal end and the fixation portion is a radially compressing semi-circular clamp adapted to fit within the collar and engage the trial stem.

17. The apparatus of claim 1, wherein the fixation portion is a compressible liner adapted to fit in the distal end of the body and engage the trial stem.

18. The apparatus of claim 5, wherein the trial stem has a medial fin and the first finger and the second finger engage the medial fin.

19. An apparatus for securing a trial stem in a medullary canal of a resected humerus, comprising:
a) a body having a proximal end and a distal end, the body adapted to receive a trial stem and adapted to be received in the medullary canal;
b) a fixation portion for engaging the trial stem, the fixation portion comprising:
a first capture member attached to the body having a first aperture;
a second capture member having a second threaded aperture; and
a first tension bolt, wherein the first tension bolt is adapted to extend through the first aperture and thread through the second aperture such that when the tension bolt is tightened the second capture member moves toward the first capture member to engage the trial stem; and
c) a trial stem.

20. The apparatus of claim 16, wherein the first capture member comprises a first finger and the second capture member comprises a second finger and the trial stem is engaged between the first finger and the second finger.

21. The apparatus according to claim 17, wherein the trial stem has a first lateral fin and a second lateral fin and the first finger engages the first lateral fin and the second finger engages the second lateral fin.

22. The apparatus according to claim 16, further comprising a first compression spring interposed between the first and second capture members and surrounding the first tension bolt.

23. The apparatus according to claim 16, wherein the first capture member has a third threaded aperture and the second capture member has a fourth aperture, the apparatus further comprising a second tension bolt adapted to be received by the fourth aperture and threaded through the third aperture so that when the second tension bolt is tightened the second capture member moves toward the first capture member to engage the trial stem.

24. The apparatus according to claim 20, further comprising a second compression spring interposed between the first and second capture members and surrounding the second tension bolt.

25. The apparatus of claim 20, wherein the first capture member comprises a first finger and the second capture member comprises a second finger and the trial stem is engaged between the first finger and the second finger.

26. The apparatus according to claim 22, wherein the trial stem has a first lateral fin and a second lateral fin and the first finger engages the first lateral fin and the second finger engages the second lateral fin.

27. The apparatus according to claim 16, wherein the fixation member further comprises a capture member connector connected to the first capture member, wherein the second capture member has a connector aperture adapted to slidably receive the capture member connector.

28. The apparatus according to claim 16, wherein the body comprises:
a collar at the proximal end;
a medial fin slot extending from the proximal end down the body;

a lateral fin slot extending from the proximal end down the body;

two rotation prevention fins extending from the collar down the body; and a trial stem sleeve at the distal end having an interior surface.

29. The apparatus according to claim 25, further comprising a friction liner adapted to be affixed to the interior surface of the trial stem sleeve.

30. A system for surgical replacement of a joint articulating portion of a bone, comprising:
   a) a selection of prosthetic implants each having a stem member and a head member, the stem members being of various lengths and diameters, each stem member having a first end adapted to be received within the medullary canal of a resected bone and a second end connected to the head member, the head members being of various heights and diameters adapted to approximate the size and shape of the joint articulating surface requiring replacement;
   b) a selection of trials each having a trial stem member and a trial head member, the trial stem members being of various lengths and diameters corresponding to the lengths and diameters of the prosthetic implant stem members, the trial stem members each having a first end adapted to be received within the medullary canal of a resected bone and a second end connected to the trial head member, the trial head members being of various heights and diameters corresponding to the heights and diameters of the prosthetic implant head members;
   c) a selection of fixation devices of various sizes corresponding to the lengths and diameters of the trial stem for securing the trial stem in the medullary canal, comprising:
      a body having a proximal end and a distal end, the body adapted to be received in the bone and adapted to receive the trial stem; and
      a fixation portion attached to the body for engaging the trial stem;
   d) a trial fixation device driver for inserting the fixation device and attached trial stem in the medullary canal; and
   e) a trial fixation device extractor for removing the fixation device from the medullary canal.

31. The system according to claim 30, wherein the prosthetic implant is modular and the stem member and the head member are separate and adapted to be coupled together.

32. The system according to claim 30, wherein the trial is modular and the trial stem member and the trial head member are separate and adapted to be coupled together.

33. The system of claim 30, wherein the fixation portion uses a clamping mechanism to engage the trial stem.

34. The system of claim 30, wherein the fixation portion comprises:
   a first capture member attached to the body;
   a second capture member; and
   a first fastener, wherein the first fastener is adapted to engage the second capture member and move the second capture member towards the first capture member to engage the trial stem.

35. The system of claim 34, wherein the first capture member has a first aperture; the second capture member has a second threaded aperture; and the first fastener is a first tension bolt adapted to extend through the first aperture and thread through the second aperture such that when the first tension bolt is tightened the second capture member moves toward the first capture member.

36. The system of claim 35, wherein the first capture member comprises a first finger and the second capture member comprises a second finger and the trial stem is engaged between the first finger and the second finger.

37. The system according to claim 36, wherein the trial stem has a first lateral fin and a second lateral fin and the first finger engages the first lateral fin and the second finger engages the second lateral fin.

38. The system according to claim 34, further comprising a first bias interposed between the first and second capture members.

39. The system according to claim 38, wherein the first bias is a first compression spring and is adapted to surround the first fastener.

40. The system according to claim 35, wherein the first capture member has a third threaded aperture and the second capture member has a fourth aperture, the fixation portion further comprising a second tension bolt adapted to extend through the fourth aperture and thread through the third aperture so that when the second tension bolt is tightened the second capture member moves toward the first capture member to engage the trial stem.

41. The system according to claim 40, further comprising a second compression spring interposed between the first and second capture members and surrounding the second tension bolt.

42. The system of claim 34, wherein the first capture member comprises a first finger and the second capture member comprises a second finger and the trial stem is engaged between the first finger and the second finger.

43. The system according to claim 42, wherein the trial stem has a first lateral fin and a second lateral fin and the first finger engages the first lateral fin and the second finger engages the second lateral fin.

44. The system of claim 30, wherein the body has a collar at the proximal end and the fixation portion is a radially compressing semi-circular clamp adapted to fit within the collar and engage the trial stem.

45. The system of claim 30, wherein the fixation portion is a compressible liner adapted to fit in the distal end of the body and engage the trial stem.

46. The system of claim 34, wherein the trial stem has a medial fin and the first finger and the second finger engage the medial fin.

47. The system according to claim 34, wherein the fixation portion further comprises a capture member connector connected to the first capture member, wherein the second capture member has a connector aperture adapted to slidably receive the capture member connector.

48. The system according to claim 34, wherein the body comprises:
   a collar at the proximal end;
   a medial fin slot extending from the proximal end down the body;
   a lateral fin slot extending from the proximal end down the body;
   two rotation prevention fins extending from the collar down the body; and
   a trial stem sleeve at the distal end having an interim surface.

49. The system according to claim 45, further comprising a friction liner adapted to be affixed to the interior surface of the trial stem sleeve.

50. A method for replacing a joint articulating portion of a bone in a patient comprising:

(a) resecting an end of the patient's bone;

(b) selecting a trial having a trial stem member and a trial head member, the trial stem member having a length and diameter that corresponds to the length of the resected bone and the diameter of the medullary canal of the resected bone, wherein the trial stem member comprises a first end adapted to be received in the medullary canal and second end coupled to the trial head member;

(c) selecting the trial head member having a height and diameter that corresponds to the height and diameter of the joint articulating surface of the bone being replaced;

(d) selecting a fixation device that corresponds to the trial stem member, the fixation device comprising a body portion adapted to be received in the resected bone and adapted to receive the trial stem member, and a fixation portion attached to the body for engaging the trial stem member;

(e) engaging the fixation device on the trial stem member;

(f) implanting the assembled trial and fixation device into the patient's bone and testing various orientations of the trial head member and trial stem member;

(g) repeating steps (c) through (f) as necessary to select a desired head size and a desired orientation;

(h) extracting the trial and fixation device from the patient;

(i) selecting a prosthesis implant head and stem that correspond to the size and shape of the trial head member and trial stem member, wherein the prosthesis implant stem comprises a first end adapted to be received within the medullary canal of the resected bone and a second end connected to the implant head;

(j) implanting the prosthesis implant into the patient's resected bone.

51. The method of claim 50, wherein the resecting an end of the patient's bone further comprises resecting a proximal humerus.

* * * * *